United States Patent
Reddy et al.

(10) Patent No.: US 7,169,793 B2
(45) Date of Patent: Jan. 30, 2007

(54) PROCESS FOR PREPARATION OF OPTICALLY PURE OR OPTICALLY ENRICHED SULFOXIDE COMPOUNDS, INCLUDING AMORPHOUS ESOMEPRAZOLE AND SALTS THEREOF

(75) Inventors: Manne Satyanarayana Reddy, Ameerpet Hyderabad (IN); Muppa Kishore Kumar, Ameerpet Hyderabad (IN); Kikkuru Srirami Reddy, Ameerpet Hyderabad (IN); Koilkonda Purandhar, Ameerpet Hyderabad (IN); Keshaboina Sreenath, Ameerpet Hyderabad (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 94 days.

(21) Appl. No.: 10/608,781

(22) Filed: Jun. 27, 2003

(65) Prior Publication Data

US 2004/0077869 A1  Apr. 22, 2004

(30) Foreign Application Priority Data

Jun. 27, 2002 (IN) .......................... 489/MAS/2002
Jun. 28, 2002 (IN) .......................... 493/MAS/2002

(51) Int. Cl.
  *A61K 31/44* (2006.01)
  *C07D 401/00* (2006.01)
(52) U.S. Cl. ................ 514/299; 514/338; 514/393; 514/395; 546/273.1; 546/273.4; 546/273.7; 546/183

(58) Field of Classification Search ................ 514/338, 514/393, 299, 395; 546/273.4, 183, 273.1, 546/273.7
See application file for complete search history.

(56) References Cited

U.S. PATENT DOCUMENTS 6,262,085 B1 * 7/2001 Whittle et al. .............. 514/338
6,369,087 B1   4/2002 Whittle et al.

FOREIGN PATENT DOCUMENTS

| WO | 9602535 | 2/1996 |
| WO | 9828294 | 7/1998 |
| WO | 9854171 | 12/1998 |

OTHER PUBLICATIONS

Eberle, D. et al. "Chiral resolution of pantoprazole sodium and related sulfoxides by complex formation with bovine serum albumin in capillary electrophoresis" Journal of Chromatography A, 759, (1997) pp. 185-192.
Komatsu N. et al. "Kinetic Resolution of Sulfoxides Catalyzed by Chiral Titanium-Binaphthol Complex" J. Org. Chem. 58, (1993) pp. 7624-7626.

* cited by examiner

*Primary Examiner*—Thomas McKenzie
*Assistant Examiner*—Raymond Covington
(74) *Attorney, Agent, or Firm*—Robert A. Franks; Edward D. Pergament; Milagros A. Cepeda

(57) ABSTRACT

A process of preparation of optically pure or optically enriched isomers of omeprazole and structurally related sulfoxides is provided. Also provided are an amorphous form of esomeprazole, as well a pharmaceutical composition containing it and a method of using it for treatment of gastric disorders.

57 Claims, 1 Drawing Sheet

PROCESS FOR PREPARATION OF OPTICALLY PURE OR OPTICALLY ENRICHED SULFOXIDE COMPOUNDS, INCLUDING AMORPHOUS ESOMEPRAZOLE AND SALTS THEREOF

CROSS REFERENCE TO RELATED APPLICATIONS

This application claims benefit of the filing date of Indian Patent Application No. 489/MAS/2002, filed Jun. 27, 2002 and Indian Patent Application No. 493/MAS/2002, filed Jun. 28, 2002, the contents of both of which are expressly incorporated herein by reference in their entirety.

FIELD OF INVENTION

This invention relates to a process for preparation of single enantiomers of organic sulfoxides, such as omeprazole and structurally related compounds, as well as their salts and hydrates. Specific salts of the resulting enantiomerically pure or enantiomerically enriched sulfoxides, as well as a method of their use, are also provided.

BACKGROUND OF THE INVENTION

Omeprazole and structurally similar sulfoxide compounds are known inhibitors of gastric acid secretion and are used as anti-ulcer agents. The sulfur atom of the sulfoxide group in asymmetrically substituted sulfoxides is chiral. Therefore, omeprazole and related sulfoxides exhibit optical isomerism at the sulfur atom of the sulfoxide. In fact, omeprazole exists as a pair of enantiomers; the S (−) enantiomer is referred to as esomeprazole.

Certain analytical and preparative methods for separation of the enantiomers of omeprazole are known in the art. For example, a reaction between a 6-methoxy analogue of omeprazole with R-mandelic acid in chloroform results in a diastereomeric mixture which may be separated by reverse phase chromatography. Preparation of a single enantiomer or an enantiomerically enriched omeprazole by asymmetric oxidation of a pro-chiral sulphide is also known. If a salt of the sulfoxide is desired, it may be obtained, for example, by a reaction with a corresponding alkaline or earth alkaline base.

Nevertheless, there is still a need for new processes of preparation of substantially optically pure or optically enriched isomers of sulfoxide compounds, as well as fore the resulting compounds, their salts, and their hydrates.

SUMMARY OF THE INVENTION

In accordance with one aspect, the invention provides a process for enantioselective preparation of single enantiomers of sulfoxide compounds and their pharmaceutically acceptable salts and hydrates. The sulfoxide compounds suitable as substrates for the process of this aspect of the invention include, for example, such pharmaceutically useful compounds as omeprazole, lansoprazole, pantoprazole, pariprazole, and leminoprazole. Thus, in this aspect, a process for preparation of a sulfoxide compound that is substantially optically pure or optically enriched is provided, and includes a) providing, in an organic solvent, a starting material that is a mixture of optical isomers of the sulfoxide group-containing compound of the structure

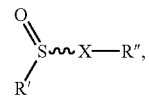

or a salt thereof, the different optical isomers having R and S configurations at the sulfur atom of the sulfoxide group;

b) reacting the mixture of optical isomers, in the organic solvent, with i) a coordinating agent containing a transition metal, and ii) a chelating agent, thereby each of the optical isomers forms a transition metal complex therewith at the sulfoxide group;

c) reacting the mixture of transition metal complexes with an organic acid, or a salt thereof, which is capable of forming an addition product with the transition metal complex; wherein at least one of the chelating agent or the organic acid contains a chiral center and is in a substantially enantiomerically pure form with respect thereto; thereby each of the transition metal complexes of the optical isomers forms an adduct with the organic acid or a salt thereof, the different adducts having at least one physical property in which they differ from one another;

d) separating one of the adducts from the other adduct based on the at least one different physical property;

treating the separated adduct with an external acid or base to decompose said transition metal complexation at said sulfoxide group, thereby obtaining a product that is one of the optical isomers of the sulfoxide compound in a substantially optically pure or optically enriched form;

wherein R' is

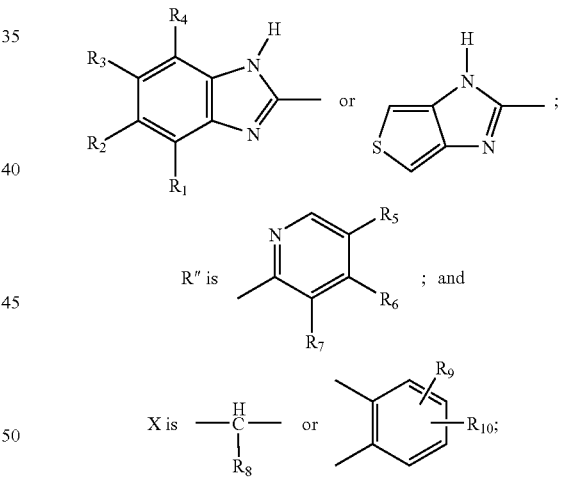

where $R_1$, $R_2$, $R_3$, and $R_4$, which may be the same or different, are each independently hydrogen, alkyl, alkoxy, halogen, halogenated alkoxy, alkylcarbonyl, alkoxycarbonyl, oxazolyl, or trifluoroalkyl;

$R_5$, $R_6$, and $R_7$, which may be the same or different, are each independently hydrogen, alkyl, halogenated alkyl, alkylthio, halogenated alkylthio, alkoxy, halogenated alkoxy, alkoxyalkoxy, dialkylamino, piperdino, morpholino, halogen, phenylalkyl or phenylalkoxy;

$R^8$ is hydrogen or lower alkyl;

$R_9$ and $R_{10}$, which may be the same or different, are each independently hydrogen, halogen, alkyl or alkoxy.

In a preferred embodiment in step c) the organic acid or salt thereof is added while stirring for about 15 minutes to about 5 hours at ambient temperature.

In a more preferred embodiment, the invention provides a specific process for preparing a substantially enantiomerically pure or enantiomerically enriched form of omeprazole and its salts. In other preferred aspect, the invention also provides an amorphous form of esomeprazole and pharmaceutical compositions containing such amorphous form, as well as a related method of treatment.

DETAILED DESCRIPTION OF THE PREFERRED EMBODIMENTS

Figure 1:
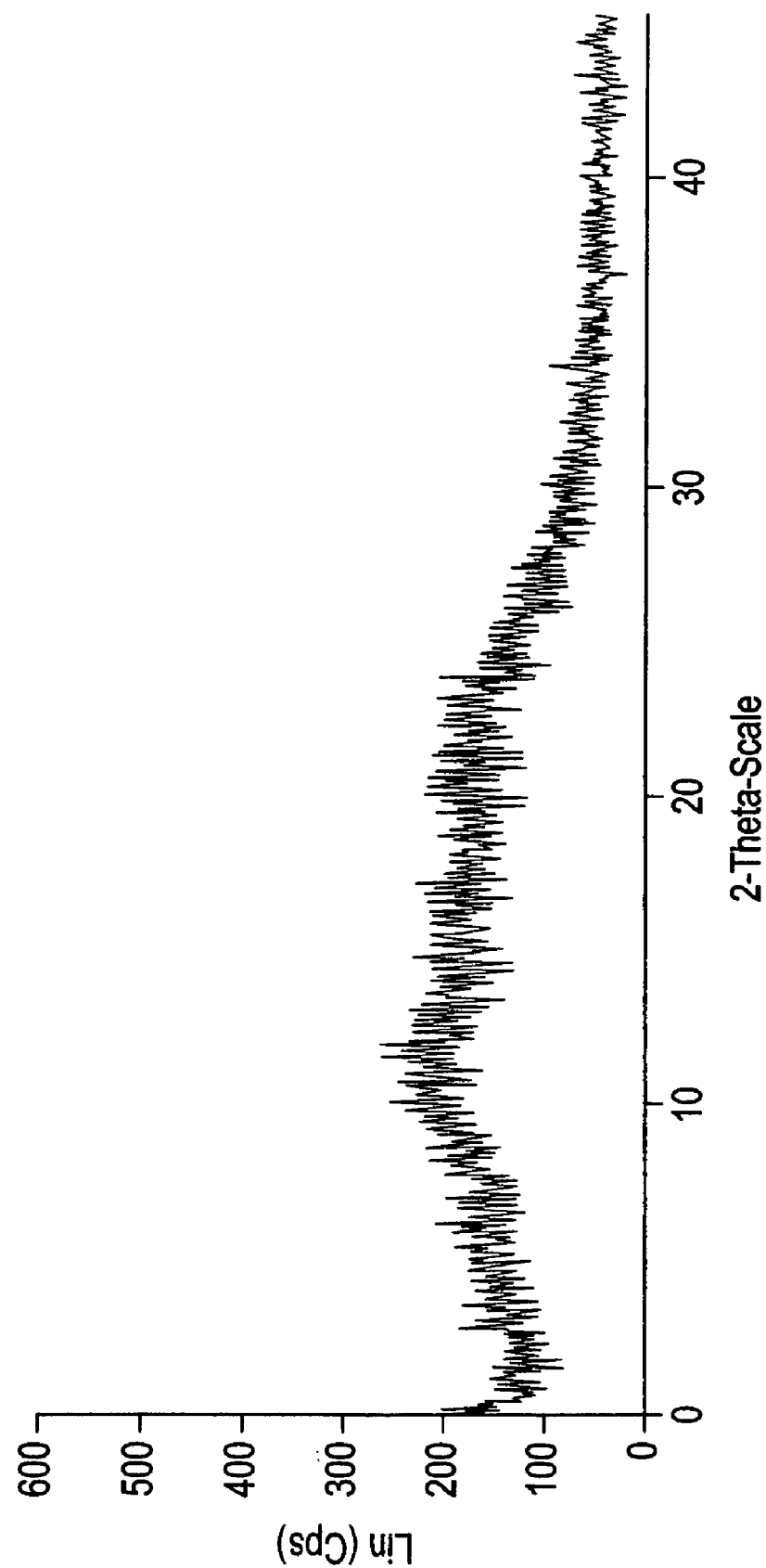
FIG. 1 shows an X-Ray Powder Diffractogram of amorphous esomeprazole.

To describe the invention, certain terms are defined herein as follows. A "compound" is a chemical substance containing one or more molecules of identical structures. A "compound" is not a mixture. A "composition" may contain one compound or a mixture of compounds. A "pharmaceutical composition" is any composition useful or potentially useful in producing physiological response in a subject to which such pharmaceutical composition is administered.

As used herein, the term "solvent" may be used to refer to a single compound or a mixture of compounds. The term "organic solvent" means a solvent conventionally understood as such in the art, including a solvent in which non-polar or hydrophobic compounds are preferentially and substantially soluble. Non-limiting examples of organic solvents include chlorinated alkanes, such as chloroform, dichloromethane, dichloroethane, and carbon tetrachloride; ketones and alkyl ketones, such as acetone, ethyl methyl ketone, methyl isobutyl ketone, and diethyl ketone; esters of organic acids, such as ethyl acetate; and nitriles, such as acetonitrile. The term "aqueous solvent" means a solvent containing water. Accordingly, the term "aqueous/organic solvent" means a mixture of water and organic solvent(s), which mixture may contain a preponderance of organic solvent or a preponderance of aqueous solvent; for example, any range from about 99.1% organic to about 0.1% aqueous to about 99.1% aqueous to about 0.1% organic, and preferably about 95% organic to about 5% aqueous. As used in this invention "external" acid or base means an acid or base which is independently added to the reaction at the indicated step, as distinct from an acid or base is already present in the reaction mixture.

In describing the compounds of the invention, certain nomenclature and terminology is used throughout to refer to various groups, substituents, and the like. In this regard, the description "$C_x$–$C_y$" refers to a chain of carbon atoms or a carbocyclic skeleton containing from x to y atoms, inclusive. The designated range of carbon atoms shall refer independently to the number of carbon atoms in the chain or the cyclic skeleton or to the portion of a larger substituent in which the chain or the skeleton is included. Also, unless stated otherwise, the terminal portion of the designated group or substituent is described first followed by a description of functionality or molecular portion that is more adjacent to the point of attachment to the rest of the molecule. In a non-limiting example, "carboxyalkyl" refers to a group having a terminal carboxy group and the point of attachment to the rest of the molecule. In an exception, "alkylhydroxy" refers to an alkyl group having a terminal or side-attached hydroxyl.

The term "alkyl," whether used alone or as a part of another group, is a group or a substituent that includes a chain of carbon atoms. The "alkyl" group or substituent may include only the chain of carbon atom, or may include a chain of carbon atoms that terminates in a non-alkyl functionality, or may include a chain of carbon atoms that is connected to the rest of the molecule through a non-alkyl functionality. The chain of carbon atoms of the alkyl groups described and claimed herein may be saturated or unsaturated, straight chain or branched, substituted or unsubstituted. In a preferred embodiment, the alkyl group is a $C_1$–$C_{16}$ alkyl group, more preferably the alkyl group is a $C_1$–$C_6$ alkyl group.

In a non-limiting example, the groups containing the carbon chains of the structures —$CH_2CH_2CH_3$, —$CHCHCH_3$, and —$CH(CH_3)CH_2CH_3$ are all "alkyl" groups as defined herein. In other non-limiting examples, the groups containing the carbon chains of the structures —$CH_2CF_2CH_3$, —$CHCHCFH_2$, —$CH_2$—$CH(OH)CH_2CH_3$, and —$CH(CH_3)CH_2CH_2COOH$ are all "alkyl" groups as defined herein. By "halogenated" alkyl is meant a group in which one or more hydrogen atoms attached to the carbon atoms of the chain is/are replaced by one or more halogens (by which is meant fluorine, chlorine, bromine, or iodine).

The term "alkoxy" refers to an oxygen ether radical containing an alkyl group, as defined previously, and an oxygen atom that connect the "alkoxy" to the rest of the molecule. In a preferred embodiment, the alkoxy group is a $C_1$–$C_{16}$ alkoxy group, more preferably a $C_1$–$C_6$ alkoxy group. The alkyl groups and alkoxy groups of the compounds described herein may be independently substituted with one or more substituents, including, but not limited to, mono-, di-, tri-, or per-halogen, including chlorine, fluorine, bromine and iodine; lower alkyl, such as a $C_1$–$C_6$ alkyl group including specifically methyl, ethyl, and propyl; lower alkoxy, such as $C_1$–$C_6$ alkoxy group including specifically methoxy, ethoxy, and propoxy; hydroxyl; amino, including mono-($C_1$–$C_6$ alkyl) amino, such as specifically methylamino, ethylamino, propylamino and the like, and di-($C_1$–$C_6$ alkyl) amino, such as specifically dimethylamino, diethylamino, methylethylamino, dipropylamino, ethylpropylamino and the like; aryl; hydroxyaryl; hydroxyalkyl; alkoxyaryl; heteroaryl, including specifically pyridyl; heterocyclyl, cyano; mercapto; nitro; and $C_1$–$C_8$ acyloxy. A group may be referred to generally or more specifically, as desired. For example, a group containing a carbon chain with one carbon-carbon double bond may be described as alkyl or alkenyl, as desired. In another non-limiting example, a group containing a carbon chain with a chloro substituent may be described as alkyl or halogenated alkyl, as desired. The term "halogenated alkoxy" is meant alkoxy group, as defined, in which one or more hydrogen atoms attached to the carbon atoms of the chain is/are replaced by one or more halogens. By "alkoxyalkoxy" is meant a lower alkoxy group-substituted lower alkoxy group such as $C_1$–$C_6$ alkoxy $C_1$–$C_6$ alkoxy group as defined, for example as methoxymethoxy.

The term "acyl", whether used alone or as part of a substituent group, refers to an organic radical derived from an organic acid by removal of the hydroxyl group. "$C_x$–$C_y$ acyl" refers to an acyl group derived from the organic acid containing a carbon chain having from x to y carbon atoms. Acyl groups may be $C_1$–$C_6$ acyl groups, non-limiting examples of acyl groups are acetyl, propionyl or benzoyl. The term "halo" or "halogen" means fluoro, chloro, bromo and iodo. Mono-, di-, tri-, and per-halo-alkyl is an alkyl radical substituted by independent replacement of the hydrogen atoms with halogen.

"Aryl", whether used alone or as part of a substituent group, is a carbocyclic aromatic radical, examples of which include, but are not limited to, phenyl, 1- or 2-naphthyl, and the like. The "aryl" groups of the compounds described herein may be substituted by independent replacement of 1 to 3 of the hydrogen atoms on the carbocyclic aromatic skeleton with substituents including, but not limited to, halogen, —OH, —CN, mercapto, nitro, amino, substituted amino, $C_1$–$C_6$ alkyl, $C_1$–$C_6$ alkoxy, $C_1$–$C_6$ alkylthio, $C_1$–$C_6$ alkylamino, halogenated $C_1$–$C_6$ alkyl, formyl, $C_1$–$C_6$ acyl, $C_1$–$C_6$ alkoxyacyl, and $C_1$–$C_6$ acylamido. Examples of aryl radicals include, but are not limited to, phenyl, naphthyl, diphenyl, fluorophenyl, methoxyethylphenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, tolyl, xylyl, and dimethylcarbamylphenyl.

Whenever the term "alkyl", "acyl", or "aryl" or any of their prefix roots appear in a description of a substituent (e.g., aralkyl, dialkylamino), it shall be interpreted as including a radical as defined above for "alkyl", "acyl", and "aryl." Whether used alone or as part of a substituent group, "heteroaryl" refers to a cyclic aromatic radical having from five to ten ring atoms of which one ring atom is selected from S, O, and N; 0–2 ring atoms are additional heteroatoms independently selected from S, O, and N; and the remaining ring atoms are carbon. The radical being joined to the rest of the molecule via any of the ring atoms, for example, pyridinyl, pyrazinyl, pyrimidinyl, pyrroyl, pyrazolyl, imidazolyl, thiazolyl, oxazolyl, isoxazolyl, thiadiazolyl, triazolyl, oxadiazolyl, thienyl, furanyl, quinolinyl, isoquinolinyl, and the like. The heteroaryl group may be substituted by independent replacement of 1 to 3 of the hydrogen atoms on the carbocyclic aromatic skeleton with substituents including, but not limited to, halogen, —OH, —CN, mercapto, nitro, amino, substituted amino, $C_1$–$C_6$ alkyl, $C_1$–$C_6$ alkoxy, $C_1$–$C_6$ alkylthio, $C_1$–$C_6$ alkylamino, halogenated $C_1$–$C_6$ alkyl, formyl, $C_1$–$C_6$ acyl, $C_1$–$C_6$ alkoxyacyl, and $C_1$–$C_6$ acylamido. By phenylalkyl is meant a phenyl group linked to the parent molecule via an alkyl substituent (as alkyl is defined), for example benzyl, 2-phenylethyl, 3-phenylpropyl. By phenylalkoxy is meant a phenyl group linked to the parent molecule via an alkoxy substituent (as alkoxy is defined), for example, benzoyl, 3-bromo-benzoyl, 4-benzyloxybenzoyl, 4-hydroxybenzoyl, 3,5-dibromobenzoyl. By alkylcarbonyl is meant alkyl as defined linked to the parent molecule via a carbonyl group ($R_1R_2C(O)$), for example methylcarbonyl. By alkoxycarbonyl is meant alkoxy as defined linked to the parent molecule via a carbonyl group, for example tert-butoxycarbonyl.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. The term "saturated" in reference to a heterocyclic or carbocyclic skeleton is used to describe skeletons devoid of double or triple bonds between the atoms of the skeleton.

The term "subject" includes, without limitation, any animal or artificially modified animal. As a particular embodiment, the subject is a human. The term "drug-resistant" or "drug-resistance" refers to the characteristics of a microbe to survive in presence of a currently available antimicrobial agent such as an antibiotic at its routine, effective concentration. The term "pharmaceutically acceptable" is used to define non-toxic substances generally suitable for use in human or animal pharmaceutical products.

This invention is directed to processes for preparation of sulfoxide compounds that, by virtue of the processes of this invention, are substantially optically pure or optically enriched. Intermediates in the processes of this invention are also part of this invention, as are their salts and hydrates.

In one embodiment of the process aspect of the invention, the starting material is a salt of the formula (I):

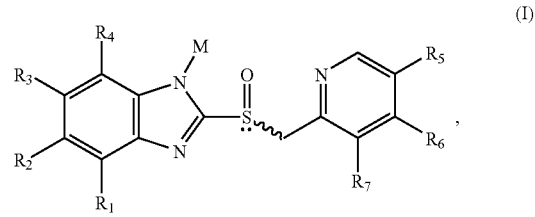

where M is an alkaline or alkaline earth metal; preferably M is sodium. In one variant, $R_1$, $R_2$, $R_3$, and $R_4$ are hydrogen. In another variant, $R_6$ may be $O(CH_2)_3OCH_3$ or $OCH_2CF_3$, especially where $R_5$ is hydrogen and $R_7$ is methyl. In a further variant, $R_1$, $R_3$, and $R_4$ are hydrogen; $R_2$ and $R_6$ are methoxy; and $R_5$ and $R_7$ are methyl, and in yet another embodiment, $R_1$, $R_3$, $R_4$, and $R_5$ are hydrogen; $R_2$ is difluoromethoxy; and $R_6$ and $R_7$ are methoxy. Specific starting materials that are suitable include omeprazole, lansoprazole, pantoprazole, and rabeprazole:

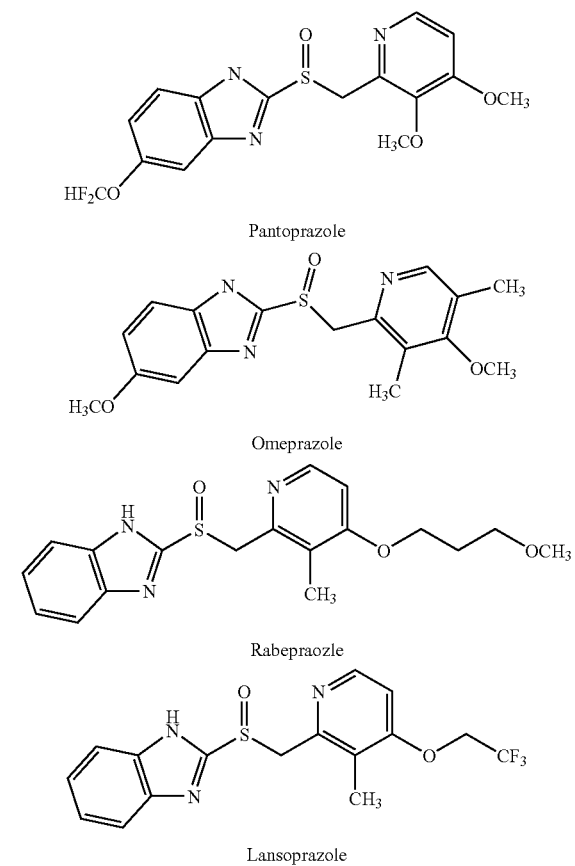

The process aspect of the invention will be illustrated using the compounds of the formula (I) as an example. Initially, the racemic mixture of sulfoxides (both R and S configurations at the sulphur atom of the sulfoxide group as indicated by the ⌇bond) is provided in an organic solvent. This may be accomplished, for example, by suspending or dissolving the compound of the formula (I) in the solvent. Suitable organic solvents are preferably polar solvents, such as esters of organic acids, nitrites, and ketones, and their mixtures, among others. More preferably, the organic solvent is alkyl ketone, such as acetone, ethyl methyl ketone, methyl isobutyl ketone, diethyl ketone, or mixtures thereof; more preferably, acetone. However, other solvents are also suitable and may be employed in the process. Thus, ethylacetate, and acetonitrile, and mixtures are also suitable.

A suspension or solution of the starting sulfoxide (I) is then treated with a coordination agent, the molecule of which contains a transition metal, and a chelating agent, resulting in the transition metal complex of the formula (II):

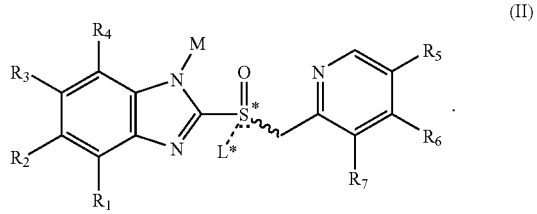

(II)

Referring to the formula (II), L indicates the portion of the molecule that includes the coordination agent and the chelating agent and the presence of chirality is indicated by the * symbol. Both optical isomers of the compound of the formula (I) form the transition metal complexes as indicated by the ⌇ bond. While the invention is not based on any specific theory, it is believed that the transition metal of the coordination agent contains empty d-orbitals in its electronic structure, thus permitting donor-acceptor interaction with the electron pair of the sulphur atom of the sulfoxide. Examples of suitable coordination agents include Ti (IV) alkoxides, such as isopropoxide, methoxide, and t-butoxide; Ti (IV) isopropoxide is the more preferred coordination agent. The chelating agent is believed to facilitate the coordination and complex formation. The more preferred chelating agent is diethyl tartrate. Preferably, the complexation proceeds in the presence of an organic base; more preferably, an organic amine, such as diisopropyl ethylamine, triethyl amine, or a mixture thereof.

The mixture of transition metal complexes of the formula (II) is then treated with an acid A to provide an adduct (III):

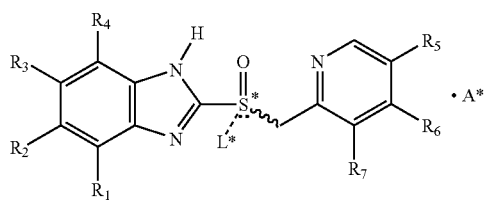

(III)

In essence, the adduct (III) is an acid addition salt of the transition metal complex (II). The preferred acids include mandelic acid, camphor sulfonic acid and derivatives, and tartaric acid; mandelic acid being more preferred. The adduct (III) is a mixture of adducts (IIIA) and (IIIB), which have R and S configurations at the sulphur atom of the sulfoxide:

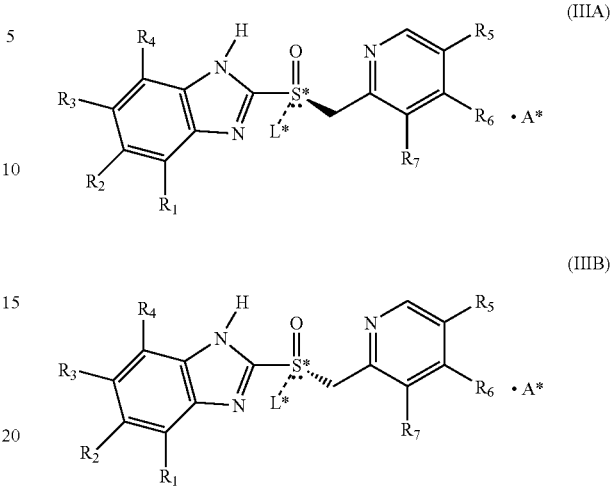

The purpose of the steps described above is to introduce at least one additional chiral center, in a substantially optically pure form, into the molecule. To this end, either the portion L or the acid L or both have at least one chiral center in the structure and is/are introduced in a substantially optically pure or optically enriched form with respect to such optical center. Preferably, both the portion L and the acid A contain chiral center(s), and are introduced in a substantially optically pure or optically enriched forms. Preferably, the portion L contains at least one chiral center; more preferably, such chiral center is introduced into the portion L via chelating agent. For example, if diethyl tartrate is used as the chelating agent, either D- or L-isomer may be used to introduce chirality into the portion L. Because of the presence of such optical center, the adduct (III) has a diastereoisomeric character. As known to those skilled in the art, diastereomers, in contrast to enantiomers, have different physical properties, for example, solubility, thus permitting separation of diastereoisomerically-related adducts (IIIA) and (IIIB). For example, one of the adducts (IIIA) or (IIIB) may have a lower solubility in the organic solvent selected for the process. The selection as to which adduct would have the lower solubility (i.e., the adduct produced from the starting material having R or S configuration at the sulphur atom of the sulfoxide) may be carried out via a selection of optical configuration of the chiral center(s) of the portion L and/or the acid A. To separate the adducts, the amount of the solvent may be, for example, selected in such a manner that one of the adducts would precipitate out of solution while the more soluble adduct may remain substantially dissolved. The less soluble adduct (for example, (the adduct (IIIA)) is filtered.

At this stage in the process, the subsequent reactions may be carried out on each adduct separately without effect on the configuration at the sulphur atom of the sulfoxide group. To obtain the sulfoxide compound itself, in a substantially optically pure form, the acid addition salt and the sulfoxide/ transition metal complexation of the isolated adduct are removed. This may be accomplished, for example, via a treatment with an external acid or base:

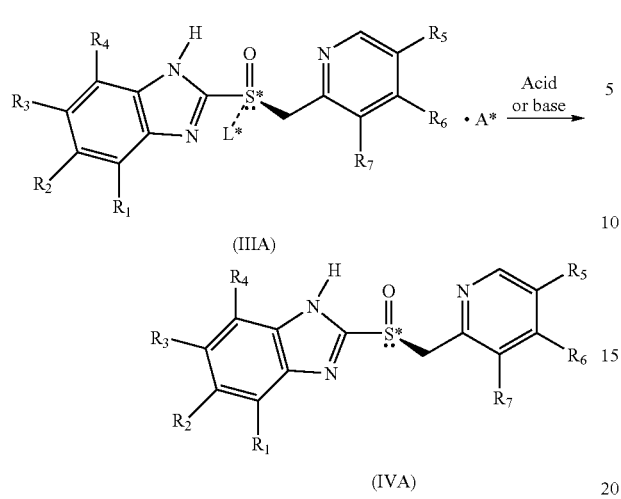

(IIIA)

(IVA)

In one preferred variant, the precipitated adduct (e.g., the adduct (IIIA)) is suspended or dissolved in a chlorinated solvent in the presence of aqueous solution of an organic or inorganic base (e.g., solution of sodium bicarbonate in water), providing the free species of the sulfoxide (the compound of the formula (IVA)) having desired configuration at the sulphur atom. The preferred chlorinated solvents in the mixture include chloroform, dichloromethane, dichloroethane, or carbon tetrachloride. The free species (IVA) may be then converted, if desired, to the desired salt (e.g., alkaline or earth alkaline salt (V)) in a manner known to those skilled in the art, such as by treatment with the corresponding base:

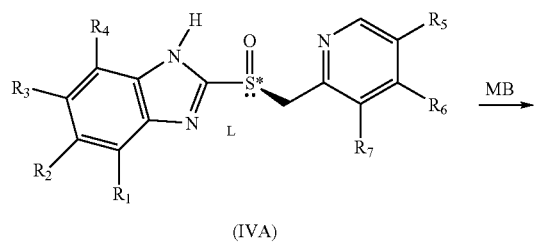

(IVA)

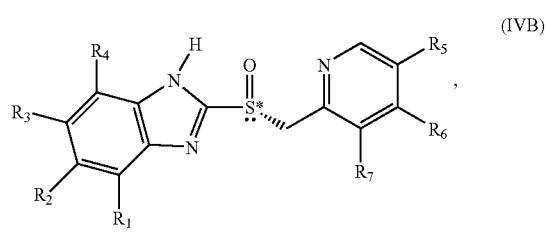

(VA)

where M is a metal and MB is the metal base, such as sodium hydroxide, potassium hydroxide, and the like. Either one of the adducts may be converted into the salt form of the sulfoxide, for example, an alkaline salt or alkaline earth salt, such as magnesium, sodium, or potassium, of one of the optical isomers of the sulfoxide compound, in a substantially optically pure or optically enriched form, also including any hydrates. The more soluble adduct (IIIB) may be converted to its own free species (IVB), which may be used in enantiomerically pure form.

(IVB)

or, if only one optical isomer is desired, may be racemized, in any way known to those skilled in the art, to obtain the starting sulfoxide (I). The racemization permits increased utilization of the material since the racemized product may be re-used in the process as described.

The preferred embodiment of the process aspect of the invention involves preparation of the (S) enantiomer of omeprazole, known as esomeprazole, and its salts. The scheme illustrates the preferred process contemplated by the inventors:

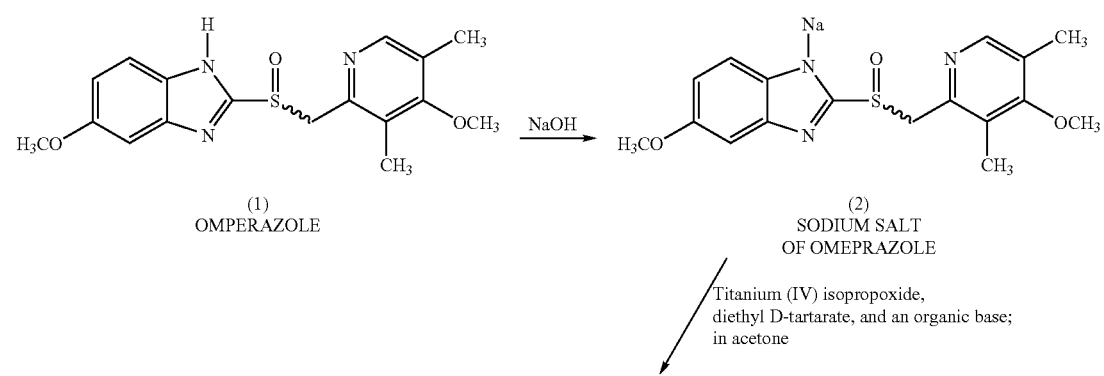

(1)
OMPERAZOLE (2)
SODIUM SALT
OF OMEPRAZOLE

Titanium (IV) isopropoxide,
diethyl D-tartarate, and an organic base;
in acetone

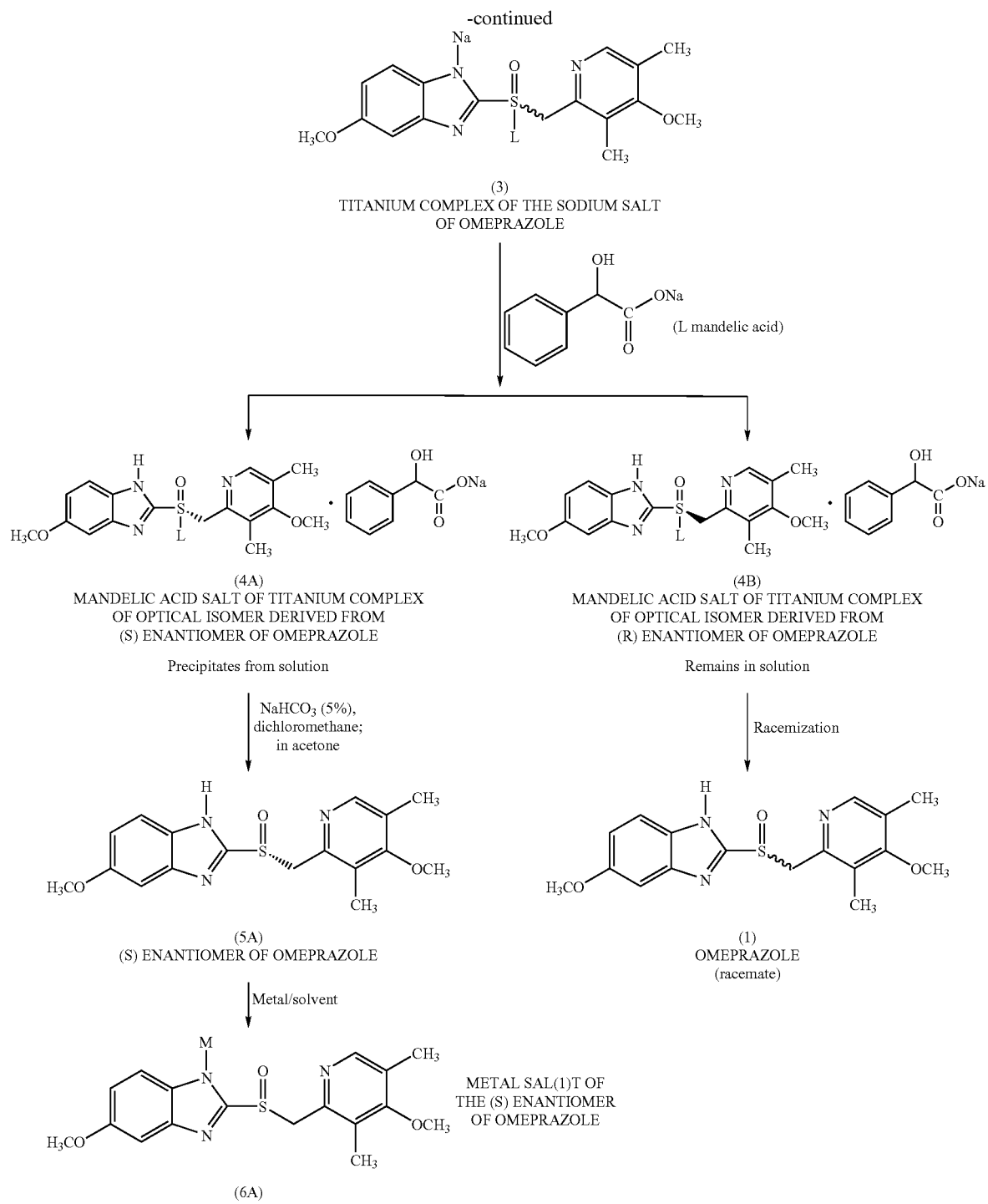

Thus, in accordance with the particular variant of the process aspect of the invention, the sodium salt of omeprazole (1) is suspended in acetone or another ketone solvent. The starting salt (2) may be purchased from a commercial source, if available. Alternatively, sodium salt of omeprazole (2) may be obtained by treating free species omeprazole with sodium hydroxide in a suitable solvent, preferably, alcohol, such as methanol or isopropanol. The suspension of racemic sodium salt of omeprazole is treated with titanium (IV) isopropoxide, diethyl D-tartrate in the presence of organic base. The preferred bases are diisopropyl ethylamine and triethylamine. Titanium isopropoxide is the coordinating agent and diethyl tartrate is the chelating agent. The resulting titanium complex (3) is then treated with L (+) mandelic acid to obtain mandelic acid salts (4A) and (4B). The salt (4A) is derived from enantiomer of omeprazole having S configuration at the sulfur atom of the sulfoxide. The salt (4B) is derived from enantiomer with R configuration. The salts (4A) and (4B) are related diastereomerically, and thus have different physical properties. The inventors have found that when diethyl D tartrate and L (+) mandelic acid are used in the process, the salt (4A) has lower solubility in ketone solvent, particularly acetone. The amount of solvent may be selected in such a manner that the less soluble salt (4A) substantially precipitates out while the more soluble salt (4B). Interestingly, the inventors also found that if enantiomer derived from R-configured isomer of omeprazole is more desired, diethyl L tartrate and D (−) mandelic acid may be used in the process, with salt derived from such R-configured isomer having lower solubility in ketone solvents. In the preferred variant, after addition of mandelic acid, the reaction mixture is maintained with stirring from at least about 15 minutes and up to about 5 hours at ambient temperature. The salt (4A) precipitates while the salt (4B) remains in solution. The separated solid salt (4A) is filtered and suspended in a mixture of aqueous base and chlorinated solvent. The preferred aqueous base is a diluted solution of sodium bicarbonate. The preferred chlorinated solvents include chloroform, dichloromethane, and carbon tetrachloride. In the basic conditions, the salt (4A) is converted to S-enantiomer of omeprazole (5A). The organic layer of the bi-phasic reaction mixture, which contains the free species of esomeprazole, is separated. The compound (5A) (esomeprazole, free species) may be isolated in any manner known to those of skill in the art.

In one variant, the organic solvent is removed, for example by vacuum distillation, and the residue of the compound (5A) is re-precipitated from a mixture of water and ketone solvent, preferably acetone. In a non-limiting example, esomeprazole residue is combined with water/acetone mixture (about 1:2 by volume) and stirred to dissolve the residue. The solution is cooled to 5–10° C., and maintain at that temperature until solid mass of esomeprazole separates. The mass is filtered and dried at 25–30° C. to a constant weight. The solid esomeprazole produced in this manner may then be dried, preferably under reduced pressure, and more referably under rotation (for example, in a Buchi rotavapor flask at about 750 mm/Hg) at a temperature of about 25° C. to about 30° C. This drying method is believed to provide a non-solvated, free-flowing solid. Esomeprazole solid obtained in such manner was found to be amorphous. FIG. 1 shows an X-ray diffractogram of this esomeprazole solid. The X-ray powder diffraction pattern of FIG. 1 was measured on a Bruker Axs, D8 advance Powder X-ray diffractometer with Cu K alpha-1 radiation source. No significant peaks are observable, which is characteristic of an amorphous material. Thus, in another preferred aspect, the invention also provides amorphous esomeprazole. If desired, the amorphous esomeprazole may then be converted into pharmaceutically-acceptable salts, such as magnesium, sodium, or potassium and their hydrates.

In another variant, the free species compound (5A) may be converted to a salt (6A). For example, the solvent may be removed and the residue of the compound (5A) may be treated with an alkali base in a manner known to those skilled in the art. Also, the residue may be treated with a free earth alkaline metal, preferably, in alcoholic solvent to obtain a desired salt of the metal. In a non-limiting example, magnesium salt of esomeprazole, believed to be in a trihydrate form, may be obtained as follows. A magnesium metal is suspended in methanol in the presence of dichloromethane; the mass is cooled to 5–10° C., and compound (5A) is added. After salt formation is complete, the reaction mixture is mixed with large quantity of water and the mixture is stirred until the solid mass of the magnesium salt of esomeprazole (compound (6A) when M is magnesium) separates from the liquid phase. The solid mass is filtered, re-dissolved in methanol and filtered again to remove unreacted magnesium metal. The solvent is removed and the residue is crystallized from acetone at 5–10° C. to afford magnesium salt of esomeprazole trihydrate.

Referring again to the scheme, the adduct (4B) remains in solution. If desired, the adduct (4B) may be converted to R enantiomer of omeprazole in the same manner as the adduct (4A). Thereafter, the R enantiomer may be racemized to omeprazole (1), which then can be used in the process.

The process as described, or portions thereof, may be repeated to improve the optical purity of the product sulfoxides. The process may be used to produce sulfoxide products, such as the magnesium trihydrate salt of the S enantiomer of omeprazole, at an optical purity and in enantiomeric excess greater than about 97%, preferably, greater than about 98%, more preferably, greater than about 98.5%, and, yet more preferably, greater than about 99%. As noted earlier, the nature of the reagents may be used to vary the principal product of the process. For example, in a particular variant, to obtain esomeprazole, diethyl-D-tartrate and L mandelic acid are preferably used; while diethyl L tartrate and D mandelic acid are used to obtain the R enantiomer of omeprazole. Examples of single or enriched enantiomeric sulfoxides salts and hydrates that may be synthesized by the process of the invention are the R (−) enatiomer of omeprazole, its pharmaceutically acceptable salt and their hydrates, the S (+) enatiomer of omeprazole, its salt and their hydrates, the magnesium salt of the S (+) enantiomer of omeprazole and its hydrate, the sodium salt of the S (+) enantiomer of omeprazole and its hydrate, the potassium salt of the S (+) enantiomer of omeprazole and its hydrate, the magnesium salt of the R (−) enantiomer of omeprazole, the sodium salt of the R (−) enantiomer of omeprazole and its hydrate, the potassium salt of the R (−) enantiomer of omeprazole and its hydrate, and the magnesium trihydrate salt of the R (−) enantiomer of omeprazole, among many others.

Pharmaceutical compositions that include one or more compounds obtained by the process aspect of the invention are also provided. In particular, in one variant, a pharmaceutical composition that includes the amorphous esomeprazole produced as described above is also provided. In addition to the active compound, the pharmaceutical composition includes one or more pharmaceutically acceptable excipients, which ordinarily lack pharmaceutical activity, but have various useful properties which may, for example, enhance the stability, sterility, bioavailability, and ease of formulation of a pharmaceutical composition. The excipients may be solid, semisolid, or liquid, and may be formulated with the compound in bulk, but ultimately in the form of a unit-dose formulation (i.e., a physically discrete unit containing a specific amount of active ingredient) such as a tablet or capsule. The pharmaceutical composition of this aspect of the invention may include, in addition to a compound of this invention, one or more active pharmaceutical compounds.

Generally, the pharmaceutical composition of the present invention are prepared by uniformly admixing the active ingredient with liquid or solid carriers and then shaping the product into the desired form. The pharmaceutical compositions may be in the form of suspensions, solutions, elixirs, aerosols, or solid dosage forms. Because of their ease of administration, tablets and capsules represent the most advantageous oral dosage unit form, in which case solid pharmaceutical carriers are employed.

The more preferred oral solid preparation is a tablet. A tablet may be prepared by direct compression, wet granulation, or molding, of the amorphous form of esomeprazole with a carrier and other excipients in a manner known to those skilled in the art. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made on a suitable machine, a mixture of the powdered compound moistened with an inert liquid diluent are suitable in the case of oral solid dosage forms (e.g., powders, capsules, and tablets). If desired, tablets may be coated by standard techniques. The amorphous form of esomeprazole described herein may be formulated into typical disintegrating tablet, or into a controlled or extended release dosage forms. Examples of suitable controlled release formulation vehicles are disclosed in U.S. Pat. Nos. 3,845,770; 3,916,899; 3,536,809; 3,598,123; and 4,008,719, the disclosures of which are hereby incorporated by reference in their entirety.

The pharmaceutical composition of this invention are contemplated in various formulations suitable for various modes of administration, including but not limited to inhalation, oral, rectal, parenteral (including subcutaneous, intradermal, intramuscular, intravenous), implantable, intravaginal and transdermal administration. The most suitable route of administration in any given case depends on the duration of the subject's condition, the length of treatment desired, the nature and severity of the condition being treated, and the particular formulation that is being used. The formulations may be in bulk or in unit dosage form, and may be prepared by methods well known in the art for a given formulation.

The amount of active ingredient included in a unit dosage form depends on the type of formulation in which the active ingredient is presented. A pharmaceutical composition will generally contain about 0.1% by weight to about 99% by weight of active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories, and tablets, each containing a pre-determined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. The amount of active ingredient per unit dosage of solid formulations is preferably from about 5 mg to 60 mg, in particular about 8 to 10 mg, about 16 to 20 mg, and about 32 to 40 mg. For liquid oral formulations, a preferable amount is from about 2% by weight to about 20% by weight. Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pH-adjusting agents, and colorants. Examples of carriers include celluloses, modified celluloses, cyclodextrins, starches, oils, polyols, sugar alcohols and sugars, and others. For liquid formulations sugar, sugar alcohols, ethanol, water, glycerol, and poyalkylene glycols are particularly suitable, and may also be used in solid formulations. Cyclodextrins may be particularly useful for increasing bioavailability. Formulations for oral administration may optionally include enteric coatings known in the art to prevent degradation of the formulation in the stomach and provide release of the drug in the small intestine.

Formulations suitable for buccal or sub-lingual administration include lozenges comprising the active compound in a flavored base, usually sucrose and acacia or tragacanth, although other agents are also suitable, and pastilles comprising the compound in an inert base such as gelatin and glycerin or sucrose and acacia.

Formulations of the present invention suitable for parenteral administration comprise sterile aqueous and non-aqueous injection solutions of the active compound, preferably isotonic with the blood of the intended recipient. The amount of active ingredient is preferably a concentration of from about 0.1% by weight to 10% by weight. These preparations may contain, among other ingredients, antioxidants, buffers, bacteriostats, and solutes that render the formulation isotonic with the blood of the intended recipient. Aqueous and non-aqueous sterile suspensions may include, among others, suspending and thickening agents. The formulations may be presented in unit-dose or multi-dose containers, e.g., sealed capsules and vials, and may be stored in a freeze-dried or lyophilized condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, e.g., cocoa butter, and then shaping the resulting mixture.

Formulations suitable for transdermal delivery include ointments, creams, lotions, and oils and contain well-known pharmaceutically and cosmetically suitable ingredients. Bases for such formulations include for example alcohols, lanolin, petrolatum, paraffin, polyethylene glycol, emulsifiers, penetration enhancing agents, and oleaginous vehicles such as oils. Skin patches may also be used, typically consisting of a fabric or paper base impregnated with a suitable dose in a transdermal formulation. Formulations suitable for transdermal administration may also be delivered by iontophoresis, and typically take the form of an optionally buffered aqueous solution of the active compound.

In another aspect, the invention also provides a method of treatment using the compounds and the pharmaceutical compositions described herein. The compounds and compositions of this invention may be administered to a subject in an amount effective to reduce secretion of gastric acid by that subject. Further, the compounds and compositions of this invention may be administered to a subject for treating a disorder caused by gastric acid secretion by administering to a subject an amount effective to reduce gastric acid secretion by said subject.

The compounds and compositions described herein may be used for treatment of various specific disorders or conditions related to gastric acid secretions and others conditions known to be suitable for treatment by sulfoxide compounds described. Certain of the compounds may be useful, for example, with respect to treatment of Parkinson's-related bradyphremia, elevated intraocular pressure, schizophrenia, infections (especially by gram-negative bacteria, microaerophilic bacteria, *Campylobacter* species), and inflammation (in particular related to lysosomal enzymes), ulcers (including those caused by *H. pylori*), heartburn, gastro-esophageal reflux, esophagitis, hypersecretory conditions (e.g., Zollinger-Ellison, endocrine adenoma, systemic mastocytosis), gastritis, duodenitis, dyspepsia, acute gastrointestinal bleeding (especially upper), for patients on NSAID therapy or in intensive care, to reduce or prevent gastric acid aspiration and stress ulceration, psoriasis and lysosomal enzyme problems, and infections such as those caused by *H. pylori*.

Although it is possible to use compounds and compositions of this invention to prevent secretion of gastric acid by establishing a dosage level effective to do so, such treatment would only be applicable in special cases, since to alleviate or eliminate most of the conditions discussed above which are treated with the compounds of this invention, gastric acid secretion should not be eliminated altogether, but only reduced in amount or duration. In general, the treatment may be determined to alleviate, to eliminate, or to prevent a given condition based on factors determinable by a skilled physician as discussed below in the context of determining an effective amount for dosage.

By subject is meant a human or an animal, preferably human. Animals contemplated by this invention include any animal safely treatable by compounds of this invention, preferably mammals such as bovines, ovines, caprines, equines, felines, canines, rodents, leporids, and other mammalian farm and zoo animals or domestic pets.

The effective amount (i.e., dosage) of active compound for treatment will vary depending on the route of administration, the condition being treated, its severity, and duration, and the state and age of the subject. A skilled physician will monitor the progress of the subject and will adjust the dosage accordingly, depending on whether the goal is to eliminate, alleviate, or prevent a given condition. Generally, the starting dosage may be low, but must at least start from the low end of the effective range, and in cases of severe ulcers it may be increased, and the active substance may be administered as maintenance therapy. The dosage of the active compound may be towards the high end of the effective range, or if needed even higher, but must always be considered in proportion to the subject's weight. Depending on the solubility of the particular formulation of active compound administered, the daily dose may be divided among one or several unit dose administrations. Administration of the active compounds may be carried out therapeutically, i.e. as a rescue treatment, or prophylactically, and may be safely maintained for prolonged periods of time. One skilled in the art will take such factors into account when determining dosage. In general oral and parenteral dosages will be in the range of about 5 to about 350 to 400 mg per day of active ingredient, preferably about 8 mg to about 60 mg, most preferably about 10 mg to about 40 mg.

The examples proved below are illustrative and are not intended to limit the scope of the claimed invention.

REFERENCE EXAMPLE

Preparation of Omeprazole Sodium

Sodium hydroxide flakes (12.8 grams) were dissolved in methanol (100 ml) and stirred until complete dissolution. Isopropyl alcohol (900 ml) was added, and the reaction mixture cooled to 25–30° C. The solution was filtered through a hi-flow bedded funnel, and washed with isopropyl alcohol (100 ml). Omeprazole (100 grams) was added to the clear filtered solution at ambient temperature, and stirred for 1–2 hours. The isolated product was filtered and washed with isopropyl alcohol (200 ml), followed by petroleum ether (200 ml), and dried at atmospheric temperature to afford the sodium salt of Omeprazole. Weight: 100 grams.

EXAMPLE 1

Preparation of Mandelic Acid Titanium Complex Salt of Esomeprazole

Omeprazole sodium (100 grams) was suspended in acetone (1.2 liter), and diethyl D-tartrate (56.0 grams), Titanium (IV) isopropoxide (40.0 grams) and triethylamine (82.0 grams) were added sequentially at a temperature of 35–40° C. L(+) Mandelic acid (41.5 grams) was then added, and further stirred for 15–30 minutes. A solid mass separated and was filtered, and washed with acetone (500 ml) to afford the title compound. The product had the following characteristics. Weight: 80.0 g; chiral Purity: 99.78%.

EXAMPLE 2

Preparation of (−)-5-methoxy-2-[[4-methoxy-3,5-dimethyl-2-pyridinyl)methyl]sulphinyl]-1H-benzimidazole Mandelic acid titanium complex salt of Esomeprazole obtained as described in Example 1 (75.0 grams) was suspended in a mixture of dichloromethane (375 ml), and 5% sodium bicarbonate solution (375 ml), further stirred for 15–30 minutes. The dichloromethane layer was separated from the resulting solution, and the solvent was distilled off completely to get the title compound as a residual mass. The characteristics of the thus resulting product were as follows. Weight: 37.0 g. Chiral Purity: 99.85%.

EXAMPLE 3

Preparation of (−) 5-methoxy-2-[[4-methoxy-3,5-dimethyl-2-pyridinyl)methyl]sulphinyl]-1H-benzimidazole Magnesium Trihydrate Salt Magnesium metal (1.33 grams) and Dichloromethane (3.7 ml) were added to methanol (111 ml) and stirred for 1–2 hours. The mass was cooled to a temperature of 5–10° C., esomeprazole obtained in Example 2 (37.0 grams) and methanol (111.0 ml) were added accompanied by stirring for 15–30 minutes. The reaction mass was decomposed into water (666 ml) at a temperature of 5–10° C. over a period of 45–60 minutes, and then further stirred for 30–45 minutes to separate the solid mass. The solid mass was filtered, and washed with water (222 ml). The thus obtained compound was dissolved in methanol (222 ml), and filtered off the solution to separate any excess magnesium. The solvent was removed from the filtrate to get the residual mass. The residual mass was crystallized in Acetone (278 ml) at a temperature of 0–5° C. to afford optically pure Esomeprazole magnesium trihydrate salt. The resulting product had the following characteristics. Weight: 11.5 g. Chiral Purity: ~100%. Optical rotation: −125° (c=0.5% methanol)

The (−) enantiomer of Omeprazole magnesium dihydrate salt was prepared as above employing a controlled drying process.

EXAMPLE 4

Preparation of (−)-5-Methoxy-2-[[4-methoxy-3,5-dimethyl-2-pyridinyl)methyl]sulphinyl]-1H-benzimidazole Sodium Trihydrate Salt Sodium hydroxide flakes (4.5 grams) were added to methanol (50 ml) and stirred for 15–30 minutes. The mass was cooled to a temperature of 5–10° C., esomeprazole obtained as in Example 2 (25.0 grams), and methanol (100.0 ml) were added with stirring for 30–60 minutes. The solvent was expelled off completely from the reaction solution. Di-isopropyl ether (150 ml) was added to the residual mass and further stirred for 30–60 minutes. The mass was cooled to a temperature of 0–5° C. and stirred for 30–60 minutes to separate the solid mass. The solid mass was filtered and dried at a temperature of 60–70° C. under vacuum to afford optically pure Esomeprazole Sodium trihydrate salt. The characteristics of the product are as follows. Weight: 14.5 g. Chiral Purity: 99.53 Optical rotation: +42° (c=0.5% water)

The sodium dihydrate salt of the S (−) enantiomer of Omeprazole was similarly prepared as above by a controlled drying process.

EXAMPLE 5

Preparation of (−)-5-Methoxy-2-[[4-methoxy-3,5-dimethyl-2-pyridinyl)methyl]sulphinyl]-1H-benzimidazole Potassium Salt Potassium hydroxide flakes (6.3 grams) were added to methanol (50 ml) and stirred for 15–30 minutes. The mass was cooled to a temperature of 5–10° C., esomeprazole obtained by the method of Example 2 (25.0 grams) and methanol (100.0 ml) were added accompanied by stirring for 30–60 minutes. The solvent was expelled off completely from the reaction solution. Di-isopropyl ether (150 ml) was added to the residual mass and further stirred for 30–60 minutes. The mass was cooled to a temperature of 0–5° C. and stirred for 30–60 minutes to separate the solid mass. The solid mass was filtered and dried at a temperature of 60–70° C. under vacuum to afford optically pure Esomeprazole Sodium trihydrate salt. The characteristics of the product were as follows: Weight: 12.0 grams, Chiral Purity: 100%, Optical rotation: +28.00 (c=1% water). The sodium dihydrate salt of the S (−) enantiomer of Omeprazole was prepared in the same manner shown above by a controlled drying process.

EXAMPLE 6

Preparation of (−)-5-Methoxy-2-[[4-methoxy-3,5-dimethyl-2-pyridinyl)methyl]sulphinyl]-1H-benzimidazole (in Solid Form)

Esomeprazole (20.0 grams, obtained as per Example-2) was dissolved in a mixture of acetone (100 ml) and water (200 ml), and stirred for 15–30 minutes. The pH of the mass was adjusted with caustic lye to 12 to 13 accompanied by stirring for 30–60 minutes. The reaction solution was subjected to carbon treatment at atmospheric temperature. The pH was further adjusted to 7 to 8 with acetic acid, and the reaction mass cooled to a temperature of 5–10° C. and stirred for 1–2 hours to crystallize the solid mass. The solid mass was filtered, washed with water (100 ml), and dried under vacuum at a temperature of 25–30° C. to a constant weight. The characteristics of the thus obtained product were. Weight: 7.0 g. Chiral Purity: 99.94%

EXAMPLE 7

Preparation of Mandelic Acid Titanium Complex Salt of the R (+) Enantiomer of Omeprazole Omeprazole sodium (10 grams) was suspended in acetone (120 ml), and diethyl L-tartrate (5.6 grams), Titanium (IV) isopropoxide (4.0 grams) and triethyl amine (8.2 grams) were added sequentially at a temperature of 35–40° C. D(−) mandelic acid (4.2 grams) was then added, and stirred for 15–30 minutes. The separated solid was filtered and washed with acetone (50 ml) to afford the title compound. The characteristics of the thus obtained product were as follows. Weight: 7.50 g. Chiral Purity: 98.01% (R Isomer)

The (+) enantiomer of Omeprazole and its salts, including the magnesium, sodium and potassium salts were prepared by a method similar to that mentioned in the above examples.

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A process for separating optical isomers, comprising:
   a) providing in an organic solvent a mixture of optical isomers of a sulfoxide group-containing compound of the structure:

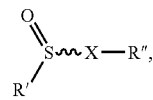

wherein R' is

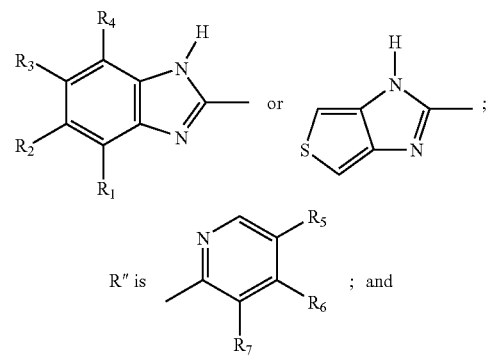

-continued

X is 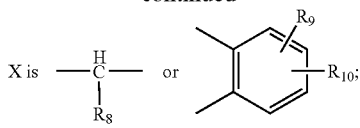

where $R_1$, $R_2$, $R_3$, and $R_4$ are each independently hydrogen, alkyl, alkoxy, halogen, halogenated alkoxy, alkylcarbonyl, alkoxycarbonyl, oxazolyl, or trifluoroalkyl;

$R_5$, $R_6$, and $R_7$ are each independently hydrogen, alkyl, halogenated alkyl, alkylthio, halogenated alkylthio, alkoxy, halogenated alkoxy, alkoxyalkoxy, dialkylamino, piperdino, morpholino, halogen, phenylalkyl or phenylalkoxy;

$R_8$ is hydrogen or lower alkyl;

$R_9$ and $R_{10}$ are each independently hydrogen, halogen, alkyl or alkoxy;

or a salt thereof, said optical isomers having R and S configurations at the sulfur atom of the sulfoxide group;

b) reacting the mixture of optical isomers with i) a coordinating agent containing a transition metal, and ii) a chelating agent, to form transition metal complexes at the sulfoxide group;

c) reacting transition metal complexes with an organic acid, or a salt thereof, to form an addition product, wherein at least one of said chelating agent and said organic acid contains a chiral center and is in a substantially enantiomerically pure form, each of said transition metal complexes of said optical isomers forming an adduct with said organic acid or a salt thereof and the different adducts having at least one physical property in which they differ from one another;

d) separating one adduct from another adduct based on said at least one physical property; and e) treating a separated adduct with an acid or base to decompose said transition metal complex at said sulfoxide group, to recover an optical isomer of the sulfoxide group-containing compound.

2. The process of claim 1, wherein said sulfoxide group-containing compound is a salt of the structure:

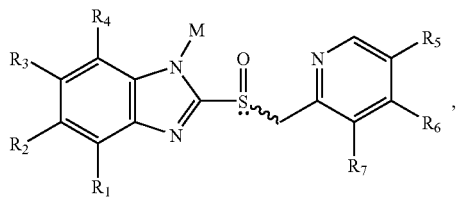

wherein M is an alkaline metal.

3. The process of claim 2, wherein M is sodium.

4. The process of claim 2, wherein $R_1$, $R_2$, $R_3$, and $R_4$ are hydrogen.

5. The process of claim 4, wherein $R_5$ is hydrogen and $R_7$ is methyl.

6. The process of claim 5, wherein $R_6$ is —O(CH$_2$)$_3$OCH$_3$.

7. The process of claim 5, wherein $R_6$ is —OCH$_2$CF$_3$.

8. The process of claim 2, wherein $R_1$, $R_3$, and $R_4$ are hydrogen; $R_2$ and $R_6$ are methoxy; and $R_5$ and $R_7$ are methyl.

9. The process of claim 2, wherein $R_1$, $R_3$, $R_4$, and $R_5$ are hydrogen; $R_2$ is difluoromethoxy; and $R_6$ and $R_7$ are methoxy.

10. The process of claim 2, wherein said step of providing comprises suspending said salt in said organic solvent.

11. The process of claim 1 wherein the reacting of step b) comprises reacting with said coordinating agent and said chelating agent in the presence of an organic base.

12. The process of claim 1, wherein said at least one different physical property is solubility of said adducts in said organic solvent.

13. The process of claim 12, wherein said step of separating said adducts comprises precipitating a less soluble adduct under conditions in which a more soluble adduct remains substantially in solution.

14. The process of claim 13, wherein said step of treating a separate adduct comprises suspending said adduct in an aqueous/organic solvent mixture under acidic or basic conditions.

15. The process of claim 14, wherein said step of treating a separate adduct comprises reacting with sodium bicarbonate.

16. The process of claim 13, further comprising decomposing a more soluble adduct to obtain an optical isomer of said sulfoxide compound different from an optical isomer obtained from a less soluble adduct.

17. The process of claim 16, further comprising racemizing an optical isomer obtain from a more soluble adduct to obtain a mixture of different optical isomers having R and S configurations at the sulphur atom of the sulfoxide group.

18. The process of claim 1, wherein said organic solvent is a ketone, an ester of an organic acid, a nitrile, or mixture thereof.

19. The process of claim 1, wherein the organic solvent is acetone, ethyl acetate, acetonitrile, or mixture thereof.

20. The process of claim 1, wherein said chelating agent is diethyl tartrate.

21. The process of claim 11, wherein said organic base is an organic amine base.

22. The process of claims 21, wherein said organic amine base is di-isopropyl ethyl amine, tri-ethyl amine, or mixture thereof.

23. The process of claim 1, wherein said coordinating agent is titanium (IV) isopropoxide.

24. The process of claim 1, wherein said organic acid is L-mandelic acid.

25. The process of claim 1, wherein said organic acid is D-mandelic acid.

26. The process of claim 10, wherein the organic solvent is an alkyl ketone.

27. The process of claim 26, wherein said alkyl ketone solvent is selected from the group consisting of acetone, ethyl methyl ketone, methyl isobutyl ketone, diethyl ketone, or mixtures thereof.

28. The process of claim 26, wherein said alkyl ketone solvent is acetone.

29. The process of claim 1, wherein the organic acid or salt thereof is added while stirring for about 15 minutes to about 5 hours at about ambient temperature.

30. The process of claim 14, wherein said aqueous/organic solvent mixture includes organic solvents selected from the group consisting of chloroform, dichloromethane, dichloroethane, carbon tetrachloride, or mixtures thereof.

31. The process of claim 30, wherein said aqueous/organic solvent mixture includes dichloromethane.

32. The process of claim 1, wherein said separation step comprises filtration.

33. The process of claim 1, further comprising converting the optical isomer obtained from one of the adducts into its salt form.

34. The process of claim 33, wherein the salt is an alkaline salt or alkaline earth salt.

35. The process of claim 33, wherein the salt is a magnesium, sodium, or potassium salt, or a hydrate thereof.

36. The process of claim 1, wherein said starting material is omeprazole.

37. The process of claim 36, wherein said chiral organic acid is L mandelic acid.

38. The process of claim 37, wherein said chelating agent is diethyl D tartrate.

39. The process of claim 36, wherein said chiral organic acid is D mandelic acid.

40. The process of claim 37, wherein said chelating agent is diethyl L tartrate.

41. The process of claim 36, producing an R enantiomer of omeprazole.

42. The process of claim 36, producing an S enantiomer of omeprazole.

43. The process of claim 41, wherein said R enantiomer of omeprazole has an optical purity greater than about 99.7%.

44. A process of separating the enantiomers of omeprazole, said process comprising:
providing a suspension of a salt of omeprazole in an alkyl ketone solvent; reacting said salt of omeprazole with titanium (IV) isopropoxide and diethyl D-tartrate in the presence of an organic base;
reacting the product of said reaction with L mandelic acid;
maintaining the reaction mixture until a solid mass separates;
wherein said solid mass is a mandelic acid salt of a titanium complex of the S enantiomer of omeprazole.

45. The process of claim 44, further comprising filtering said solid mass.

46. The process of claim 45, further comprising reacting said mandelic acid salt with an aqueous base thereby obtaining a residue, which is a free esomeprazole.

47. The process of claim 45, further comprising re-precipitating said residue from a mixture of water and acetone to obtain a solid that is an amorphous form of free esomeprazole.

48. The process of claim 46, further comprising reacting said free omeprazole with a magnesium metal in the presence of dichloromethane in an alcoholic solvent thereby obtaining a residue of a magnesium salt of esomeprazole.

49. The process of claim 48, further comprising dissolving said residue of magnesium salt of esomeprazole in acetone and lowering the temperature of said acetone solution to cause the magnesium salt of esomeprazole to precipitate therefrom.

50. The process of claim 48, wherein said alcoholic solvent is methanol.

51. The process of claim 45, wherein said ketone is acetone.

52. The process of claim 45, wherein said organic base is di-isopropyl ethyl amine, triethyl amine, or mixture thereof.

53. The process of claim 46, wherein said aqueous base is a solution of sodium bicarbonate in water.

54. The process of claim 53, wherein said sodium bicarbonate is present in said solution at a concentration of about 5% by weight.

55. A pharmaceutical composition comprising i) a therapeutically effective amount of amorphous esomeprazole produced by the process of claim 47; and ii) one or more pharmaceutically-acceptable excipients.

56. The pharmaceutical composition of claim 55, which is a solid dosage form for oral administration.

57. The pharmaceutical composition of claim 56, wherein said solid dosage form is a tablet.

* * * * *